United States Patent [19]

Baumann et al.

[11] 4,233,464
[45] Nov. 11, 1980

[54] CYCLOHEXENE CAROTINOID INTERMEDIATES

[75] Inventors: Manfred Baumann, Mannheim; Werner Hoffmann, Neuhofen, both of Fed. Rep. of Germany

[73] Assignee: BASF Aktiengesellschaft, Fed. Rep. of Germany

[21] Appl. No.: 895,629

[22] Filed: Apr. 12, 1978

[30] Foreign Application Priority Data

Apr. 20, 1977 [DE] Fed. Rep. of Germany ....... 2717502

[51] Int. Cl.$^3$ .......................................... C07C 43/303
[52] U.S. Cl. ................................... 568/591; 568/824; 568/446; 560/236; 560/259; 570/217
[58] Field of Search ........................... 260/611 V, 598; 568/668, 591

[56] References Cited

U.S. PATENT DOCUMENTS

| 2,586,305 | 2/1952 | Copenhaver | 260/598 X |
| 2,677,708 | 5/1954 | Copenhaver | 260/615 A X |
| 2,730,549 | 1/1956 | Isler et al. | 260/598 |
| 3,354,224 | 11/1967 | Redel et al. | 260/611 V |

OTHER PUBLICATIONS

Inhoffen et al., Justus Liebigs Annalen Der Chemie, vol. 598 (1956), 51–64.

*Primary Examiner*—Bernard Helfin
*Attorney, Agent, or Firm*—Keil & Witherspoon

[57] ABSTRACT

1-[3-Methyl-3,5,5-trialkoxy-pent-1-yn-1-yl]-2,6-dimethyl-cyclohex-1-enes, which may or may not be methyl-substituted in the 2- and/or 6-position, are obtained by reacting the corresponding 1-[3-methyl-but-1-yn-3-en-1-yl]-2,6-dimethyl-cyclohex-1-enes with orthoformic acid esters in the presence of acid condensing agents. The new compounds provide a new method of access to the compounds of carotinoid chemistry, especially to vitamin A, which avoids the conventional expensive synthesis via phosphorus ylide compounds.

3 Claims, No Drawings

CYCLOHEXENE CAROTINOID INTERMEDIATES

The present invention relates to new cyclohexene derivatives of the general formula I

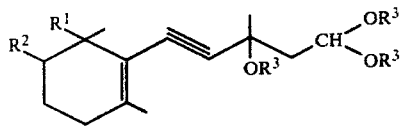

where $R^1$ and $R^2$ are hydrogen or methyl and $R^3$ is alkyl of 1 to 4 carbon atoms, and to a process for the preparation of these compounds and a process for their conversion to the aldehydes of the formula Ia:

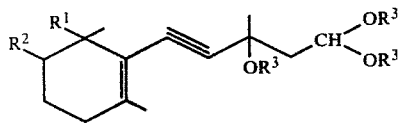

It is an object of the present invention to provide a new method, independent of the Wittig ylide synthesis, of obtaining compounds of the carotinoid series, especially vitamin A. More particularly, it is an object of the invention to provide a suitable structural unit for the synthesis of these carotinoid compounds. As used in the present specification, carotinoid compounds means the carotinoids, their derivatives and their precursors.

We have found that a cyclohexene derivative of the general formula I

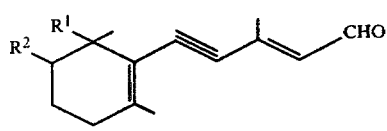

where $R^1$ and $R^2$ are hydrogen or methyl and $R^3$ is alkyl of 1 to 4 carbon atoms is obtained when a cyclohexene derivative of the general formula II

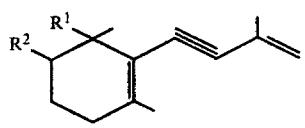

where $R^1$ and $R^2$ have the above meanings, is reacted, at from $-30°$ to $+60°$ C. and in the presence of an acid condensing agent, with an orthoformic acid ester of the general formula III

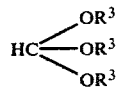

where $R^3$ has the above meaning.

The starting compounds II are new compounds which are easily obtainable in good yields by the process of German patent application P 25 58 807.2 (which does not constitute prior art and which corresponds to U.S. Pat. No. 4,088,681) by dehydrating the cyclohexanol derivatives IVa or IVb

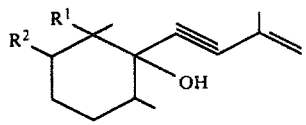

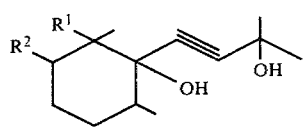

by conventional methods. IVa and IVb can in turn be prepared by condensing the cyclohexane derivatives V

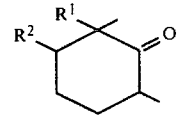

with 3-methyl-but-1-yn-3-ene are 3-methyl-but-1-yn-3-ol, respectively.

The fact that compounds II can be selectively and smoothly reacted with a commercial orthoformic acid ester to give the required product is noteworthy inasmuch as this reaction has hitherto only succeeded in the case of particular simple olefinically unsaturated compounds, eg. isobutene, styrene, indene and cyclopentadiene (cf. U.S. Pat. Nos. 2,677,707 and 2,677,708).

Suitable acid condensing agents are, in particular, strong Lewis acids, eg. $BF_3$, $AlCl_3$, $FeCl_3$, $SbCl_5$, $AlBr_3$, $CuSO_4$ and $SnCl_4$ in the free form or in the form of organic adducts, for example the etherates, eg. $BF_3.O(C_2H_5)_2$. With weaker Lewis acids, eg. $ZnCl_2$ or $TiCl_4$, the reaction takes place substantially more slowly. It is true that the reaction can also be carried out with proton acids, eg. p-toluenesulfonic acid, trichloroacetic acid, concentrated $H_2SO_4$ or HF, but according to our observations to date, the yield of I is less. The preferred condensing agents are boron trifluoride etherate and $FeCl_3$. The amount of the acid condensing agent is preferably from 0.01 to 0.1 mole per mole of III. If smaller amounts, ie. less than about 0.01 mole per mole of III, are used, the reaction takes place uneconomically slowly, whilst larger amounts of catalyst, ie. up to about 0.3 mole per mole of III, in general do not accelerate the reaction to the extent that their use would be economically justified.

Amongst the orthoformic acid esters III, trimethyl orthoformate and triethyl orthoformate are the most important because they are commercially available and are the most highly reactive, and also because the corresponding compounds I exhibit the greatest reactivity in subsequent reactions. In such subsequent reactions, all 3 of the alkoxy groups are in most cases split off, to form an en-al group. If, on the other hand, a controlled reaction at only one of these $OR^3$ groups is desired, it is advantageous to prepare compounds I with higher alkoxy groups because of the better differentiated rates at which the various alkoxy groups react, ie. the synthesis is carried out with the corresponding higher orthoformic acid esters III.

Since the Lewis acids, especially $BF_3$, are powerful isomerizing catalysts, it is advantageous to keep the concentration of the starting compound II in the reaction mixture very low, for example by carrying out the reaction in an equal to 5-fold amount of an inert diluent, eg. toluene, methylene chloride or ether, or in an excess of the orthoformic acid ester. A particularly advantageous method is to dissolve the condensing agent in the orthoformic acid ester and to add the pure or only slightly diluted compound II slowly to this solution.

Within the stated range of from $-30°$ to $+60°$ C., the best results in respect of reaction rate and yield are achieved at from $-20°$ to $+20°$ C. At lower temperatures, the formation of by-products is repressed but the reaction times are longer, whilst at higher temperatures the converse is as a rule true.

Since there is normally no reason to carry out the reaction under reduced pressure or superatmospheric pressure, it is in general effected under atmospheric pressure.

The reaction time is generally from about 2 to 50 hours.

The reaction can readily be followed by thin layer chromatography on samples of the reaction mixture. When the reaction rate has become negligible, the mixture is advantageously neutralized with an organic base, eg. ethanolamine or triethylamine, or an aqueous inorganic base, eg. an aqueous solution of $Na_2CO_3$ or $NaHCO_3$, and the compound I may be worked up by distillation in the conventional manner.

If the compound I is to be used directly for further syntheses, its purification is superfluous.

The compounds I, ie. 1-[3-methyl-3,5,5-trialkoxy-pent-1-yn-1-yl]-2,6-dimethyl-cyclohex-1-ene and its derivatives conforming to the general definition can be converted, without prior isolation, to the aldehydes of the general formula Ia $$R^2\underset{}{\overset{R^1}{\diagdown}}\diagup\diagdown\equiv\diagdown\diagup\diagdown\underset{O}{\overset{H}{C\diagup}}\quad Ia$$

in the conventional manner, by reaction with acids, eg. aqueous acetic acid, aqueous sulfuric acid, hydrochloric acid, formic acid or phosphoric acid, at from 20° to 100° C., or by reaction with superheated steam in the presence of oxalic acid or, preferably, by heating with concentrated aqueous acetic acid, buffered with sodium acetate, at 95° C., in accordance with the method described in Helv. Chim. Acta. XXXIX (1956), 2041–53, especially 2050; these aldehydes can in turn be used to prepare, for example, vitamin A, by the method shown schematically below:

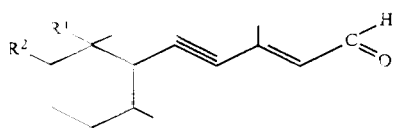

Ia $\xrightarrow{\text{Acetone}}{\text{ROH}}$

Grignard ↓ vinylation

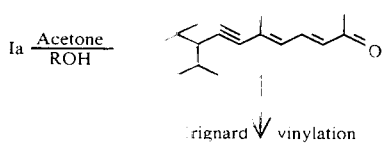

OH

↓ $SOCl_2$ (toluene + dimethylformamide)

Halogen

↓ $NaO-CO-CH_3$ $O-CO-R$

↓ Partial hydrogenation

Vitamin A ester

This provides a novel method of access to the compounds of carotinoid chemistry, which method, at the very least, supplements the conventional synthesis via phosphorus ylide compounds. A great advantage of the novel total synthesis of vitamin A is that it can be carried out without the large stoichiometric amount of toxic phosphines, which on the one hand cannot be regenerated economically from the phosphine oxides formed, and on the other hand present considerable problems of disposal without pollution of the environment.

It is true that the aldehydes Ia, which are intermediates in the above synthesis, are known (cf. J.Chem.Soc. 1949, No. 12, 3123–3126; British Patent 674,089 and U.S. Pat. No. 2,531,567), but they were not previously obtainable by an economical method, so that they could not previously be considered for industrial syntheses.

EXAMPLE 1

1-[3-Methyl-3,5,5-trimethoxy-pent-1-yl-1-yl]-2,6,6-trimethylcyclohex-1-ene 11 g (0.059 mole) of 1-[3-methyl-but-3-en-1-yn-1-yl]-2,6,6-trimethyl-cyclohex-1-ene are added in the course of from 30 to 60 minutes, at 0° C., to a solution of 85 g (0.8 mole) of trimethyl orthoformate and 5 g (0.03 mole) of $BF_3$-etherate, during which addition the reaction mixture assumes a violet color. The reaction is complete after stirring for 6 hours at 0° C., as is ascertainable from thin layer chromatograms and from the NMR or IR spectra. The reaction mixture is rendered slightly basic with about 5 g of ethanolamine and is then worked up by distillation. This gives the above product in 65% yield, based on an enyne conversion of 45%.

The compound, the structure of which can be demonstrated by IR and NMR spectroscopy, is an oily liquid of boiling point 150° C./0.02 mm Hg. Its structure was confirmed by conversion to the known aldehyde Ia.

EXAMPLE 2

1-[3-Methyl-3,5,5-triethoxy-pent-1-yn-1-yl]-2,6,6-trimethylcyclohex-1-ene

Using a method similar to that described in Example 1, 60 g (0.42 mole) of triethyl orthoformate, 5 g (0.038 mole) of anhydrous $AlCl_3$ and 25 g (0.133 mole) of the above starting compound are reacted, whilst cooling with ice, after which the reaction mixture is stirred for 20 hours at room temperature. The yield of crude product is 95% of theory, based on 65% conversion.

1H-NMR (CDCl$_3$; TMS) δ=1.09 (s) 6 protons; 1.5 (s) 3 protons; 1.0–1.6 (m) 15 protons; 1.6–2.2 (m) 5 protons; 3.6 (m) 6 protons; 4.8 (t) 1 proton.

EXAMPLE 3

1-[3-Methyl-pent-1-yn-3-en-5-al-1-yl]-2,6,6-trimethyl-cyclohex-1-ene 27.5 g of the product from Example 2 are heated with a mixture of 100 ml of glacial acetic acid, 16 g of Na acetate and 30 ml of water for 3 hours at 90° C., 200 g of water are then added and the reaction mixture is extracted with 4 times 100 ml of petroleum ether. Conventional working up by distillation gives the above aldehyde in 59% yield, based on 100% conversion.

EXAMPLE 4

80 g (0.425 mole) of 1-[3-methyl-but-3-en-1-yn-1-yl]-2,6,6-trimethyl-cyclohex-1-ene were added in the course of 10 minutes, at 0° C., to a mixture of 180 g (1.22 moles) of triethyl orthoformate and 10 g of BF$_3$.O(C$_2$H$_5$)$_2$ and the batch was stirred for 8 hours at 0° C. and 12 hours at 20° C.

The reaction was then stopped by destroying the BF$_3$ catalyst with aqueous Na$_2$CO$_3$ solution. 480 g of glacial acetic acid, 75 g of Na acetate and 140 g of water were then added to the reaction mixture and the batch was heated for 8 hours at 90° C.

This resulted in the formation of 1-[3-methyl-pent-1-yn-3-en-5-al-1-yl]-2,6,6-trimethyl-cyclohex-1-ene, which was isolated, by conventional working up, in 59% yield based on enyne converted.

EXAMPLE 5

1-[3-Methyl-3,5,5-trimethoxy-pent-1-yn-1-yl]-2,6,6-trimethylcyclohex-1-ene 88.5 g (0.47 mole) of 1-[3-methyl-but-3-en-1-yn-1-yl]-2,6,6-trimethyl-cyclohex-1-ene were added in the course of 60 minutes, at 0° C., to a mixture of 148 g (1 mole) of triethyl orthoformate and 5 g (0.032 mole) of FeCl$_3$ and the reaction mixture was then stirred for 16 hours at 20° C. Thereafter it was rendered alkaline with 70 ml of saturated sodium carbonate solution, the aqueous phase was separated off and the organic phase was dried. The NMR spectrum shows the presence of a mixture of starting material and product.

The crude product, obtained by concentrating the organic phase, was heated, by the method described in Example 3, for 3 hours with CH$_3$COOH/CH$_3$COONa/water. Subsequent working up by distillation gave 30 g of unconverted starting compound and 27 g of 1-[3-methyl-pent-1-yn-3-en-5-al-1-yl]-2,6,6-trimethyl-cyclohex-1-ene. This corresponds to a yield of 41% based on the enyne, at a conversion of 70%.

EXAMPLE 6

1-[3-Methyl-3,5,5-triethoxy-pent-1-yn-1-yl]-2,6,6-trimethylcyclohex-1-ene 32.5 g (0.173 mole) of 1-[3-methyl-but-3-en-1-yn-1-yl]-2,6,6-trimethyl-cyclohex-1-ene were added in the course of 40 minutes, at 0° C., to a mixture of 80 g (0.54 mole) of triethyl orthoformate. The reaction mixture was then stirred for 12 hours at 20° C. After working up as described in Example 1, 27.8 g of unconverted enyne and 2.2 g of the above product (identified by NMR spectroscopy) were obtained. Conversion: 15%.

We claim:

1. A cyclohexene derivative of the general formula I

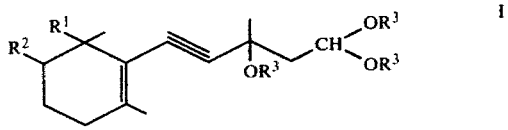

wherein R$^1$ and R$^2$ are hydrogen or methyl, and R$^3$ is alkyl of 1 to 4 carbon atoms.

2. 1-[3-Methyl-3,5,5-trimethoxy-pent-1-yn-1-yl]-2,6,6-trimethyl-cyclohex-1-ene.

3. 1-[3-Methyl-3,5,5-triethoxy-pent-1-yn-1-yl]-2,6,6-trimethyl-cyclohex-1-ene.

* * * * *